US00PP26158P3

(12) United States Plant Patent
Jones et al.

(10) Patent No.: US PP26,158 P3
(45) Date of Patent: Nov. 24, 2015

(54) ***DIASCIA* PLANT NAMED 'AURORA CHERRY BLOSSOM'**

(50) Latin Name: *Diascia×hybrida*
Varietal Denomination: Aurora Cherry Blossom

(71) Applicants: Sidney James Jones, Gwent (GB); David James Jones, Caldicot (GB)

(72) Inventors: Sidney James Jones, Gwent (GB); David James Jones, Caldicot (GB)

( * ) Notice: Subject to any disclaimer, the term of this patent is extended or adjusted under 35 U.S.C. 154(b) by 150 days.

(21) Appl. No.: 13/998,877

(22) Filed: Dec. 17, 2013

(65) Prior Publication Data

US 2015/0173288 P1 Jun. 18, 2015

(51) Int. Cl.
*A01H 5/02* (2006.01)

(52) U.S. Cl.
USPC ..... Plt./425

(58) Field of Classification Search
USPC ..... Plt./425
See application file for complete search history.

*Primary Examiner* — Keith Robinson
(74) *Attorney, Agent, or Firm* — James M. Weatherly; Bethany R. Roahrig; Cochran Freund & Young, LLC

(57) ABSTRACT

A new cultivar of *Diascia* plant named 'Aurora Cherry Blossom' that is characterized by compact upright plant habit and elongated racemose inflorescences consisting of many white colored flowers with contrasting cerise colored eyes, is disclosed.

2 Drawing Sheets

Genus and species: *Diascia×hybrida.*
Denomination: 'Aurora Cherry Blossom'.

BACKGROUND

The present invention relates to a new and distinct cultivar of twinspur, which is grown as a spring and summer flowering annual or perennial plant for use in containers, borders and in mass landscape planting. The new cultivar in the genus *Diascia* will be referred to hereinafter by the cultivar name 'Aurora Cherry Blossom'. The inventors have been interested and have collected plants of the genus *Diascia* since the early 1990s.

*Diascia*, which is native to southern Africa, provides showy annual and perennial (in mild climates) plants whose predominant flower color range in nature is in the range of soft to dark pink, also white, lavender-pink, salmon and apricot. Plants of *Diascia* which are raised from seed are inherently variable in growth habit, ranging from loose, weak plants with brittle stems to plants with significantly shorter internodes. Various breeding programs, including the inventors', have aimed to develop improvements in plant habit and also an extension of the color range into the deep pink, red or orange shades and ideally with very similar compact habits for each color.

Commencing in or around 1998, the inventors commenced a breeding project to develop a uniform series of *Diascia* which exhibit flowers held erect and above the foliage, in a range of colors, and borne on plants with compact habit. By 2003, the inventors had isolated certain seedlings which presented stiffly held longer racemes of individual flowers. Although the inventors deliberately selected and set aside parents for their presumed usefulness for immediate and future hybridization, the parents themselves were not named. The inventors estimate that approximately thirty generations of crosses preceded the selection of 'Aurora Cherry Blossom' in 2009. 'Aurora Cherry Blossom' was selected by the inventors as an individual seedling within a population of many hundreds of seedlings which flowered in that year. In general, whereas these seedlings exhibited a diverse range of plant and flower heights, habits, and colors, 'Aurora Cherry Blossom' was selected by the inventors for its combination of qualities including length of inflorescence, arrangement of individual flowers within the inflorescence, clarity of flower color, and compatibility with other candidates for a related series. The inventors consider that this combination of inflorescence characteristics is unique in the genus and that no close comparison varieties exist except for the inventors' series companion varieties 'Aurora Apricot' (U.S. Plant Pat. No. 25,451), 'Aurora Light Pink' (U.S. Plant Pat. No. 25,405) and 'Aurora Dark Pink' (U.S. Plant Pat. No. 25,719). The flowers of 'Aurora Cherry Blossom' are predominantly white in color, the flowers of the comparison series varieties are apricot, light pink and dark pink respectively. In addition, plants of 'Aurora Cherry Blossom' exhibit a tighter, shorter and more upright habit than the plants of the comparison series varieties or in comparison with any of the seedlings previously raised by the inventors, including the parents.

The first asexual propagation of 'Aurora Cherry Blossom' was conducted in 2009 by the inventors at their nursery in Newport, Gwent, United Kingdom. The method of asexual propagation used was vegetative tip cuttings. Since that time the unique and distinguishing characteristics of 'Aurora Cherry Blossom' have been determined stable, fixed, and reproduce true to type in successive generations of asexual reproduction.

SUMMARY

The following traits have been repeatedly observed and represent the characteristics of the new *Diascia* cultivar 'Aurora Cherry Blossom'. 'Aurora Cherry Blossom' has not been tested under all possible conditions and phenotypic differences may be observed with variations in environmental, climatic, and cultural conditions, without however, any difference in genotype.

1. 'Aurora Cherry Blossom' exhibits compact and erect habit.
2. The inflorescence of 'Aurora Cherry Blossom' consists of individual flowers which are arranged in an elongated triangular raceme.
3. The quantity of flowers which are borne in a single inflorescence during its life ranges between 20 and 30, of which 8 to 15 are fully open at any one time.
4. 'Aurora Cherry Blossom' exhibits spires of white colored flowers.
5. Each flower of 'Aurora Cherry Blossom' exhibits a cerise colored eye.
6. 'Aurora Cherry Blossom' blooms profusely spring through fall.
7. 'Aurora Cherry Blossom' exhibits glossy mid-green colored foliage.
8. 'Aurora Cherry Blossom' is propagated using the method of vegetative tip cuttings.
9. 'Aurora Cherry Blossom' is fast growing. A spring planted young plant fills and flowers in a 10 cm container in six to eight weeks from spring transplanting.
10. The cultural requirements of 'Aurora Cherry Blossom' are well-draining soil, full sun, and regular water.
11. 'Aurora Cherry Blossom' is suitable for use in raised beds, borders, hanging baskets, and patio containers.
12. 'Aurora Cherry Blossom' is hardy to USDA Zone 8.

BRIEF DESCRIPTION OF THE DRAWINGS

The accompanying color drawings

Figure 1:
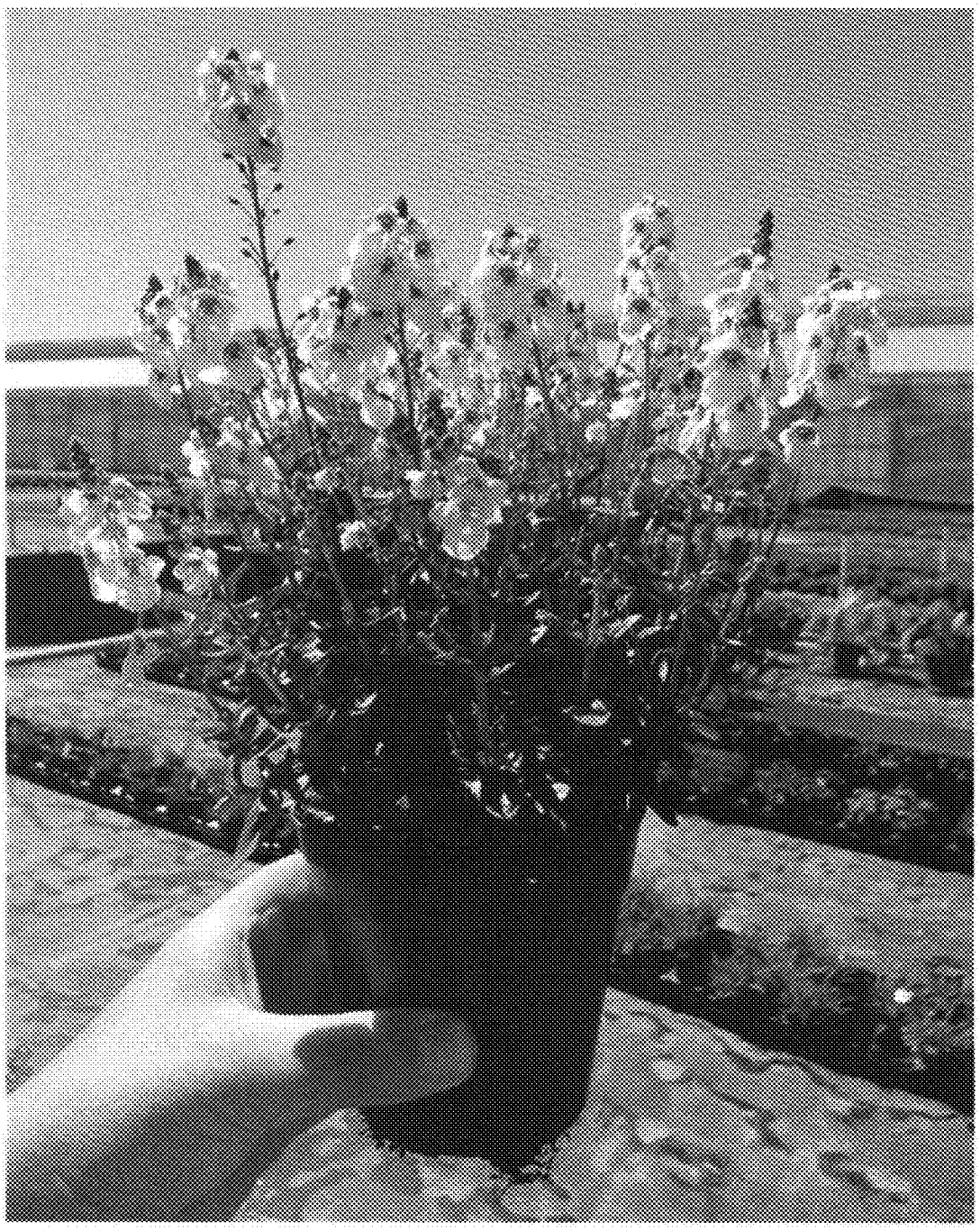
FIG. 1 and FIG. 2 illustrate the overall appearance of the new *Diascia* cultivar 'Aurora Cherry Blossom' showing the colors as true as it is reasonably possible to obtain in colored reproductions of this type. Colors in the drawings may differ from the color values cited in the detailed botanical description, which accurately describes the actual colors of the new variety of *Diascia* named 'Aurora Cherry Blossom'.

The drawing labeled as FIG. 1 depicts one whole plant of 'Aurora Cherry Blossom' which is growing and flowering in a 10 cm diameter container in mid-summer out of doors in Oxnard, Calif. The illustrated plant was started from a rooted cutting approximately 4 months previously and maintained in a frost-free greenhouse until placing outdoors in spring.

Figure 2:
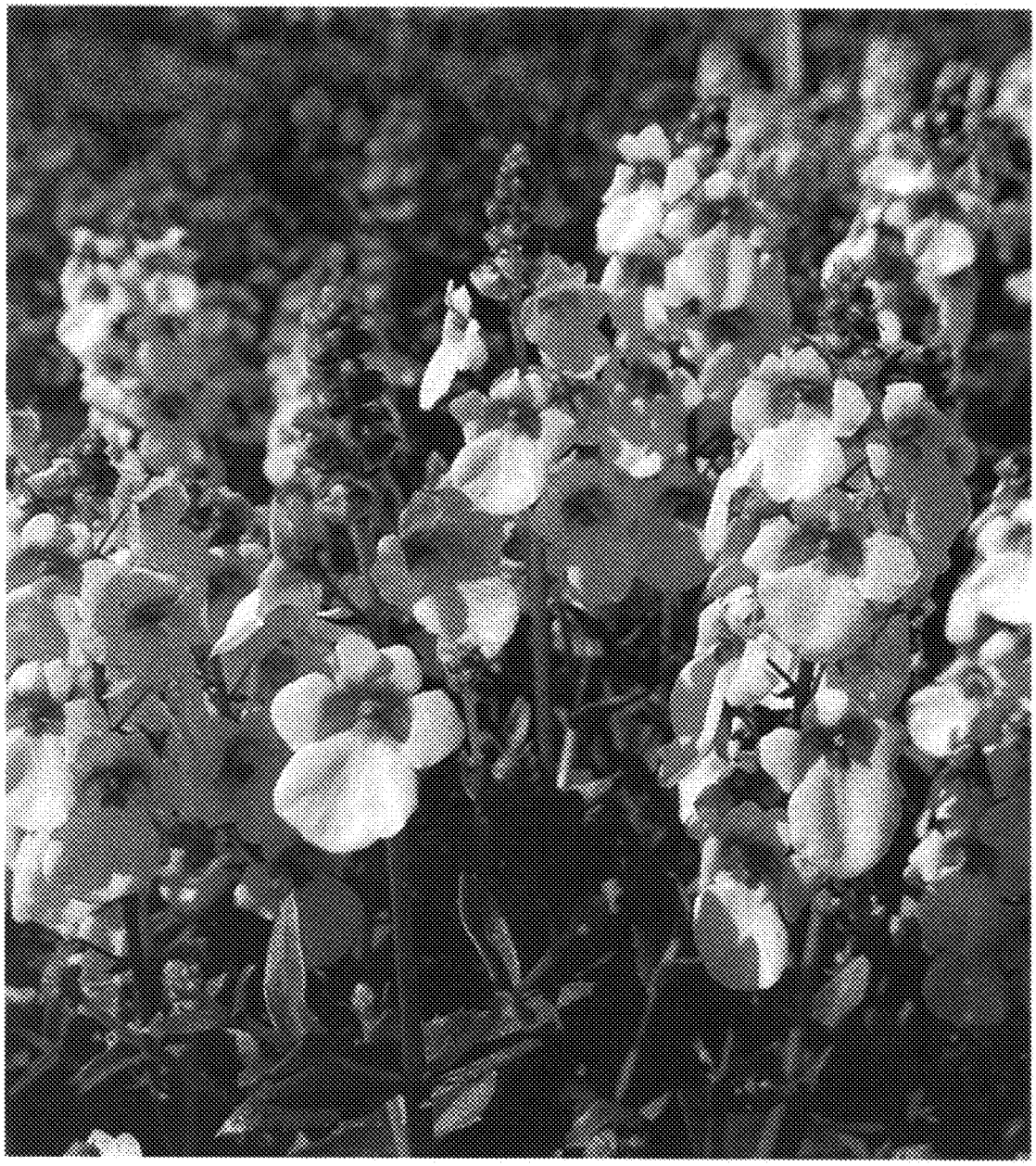

The drawing labeled as FIG. 2 illustrates the racemose inflorescence of 'Aurora Cherry Blossom' together with the individual white colored flowers and contrasting cerise colored eyes.

Both drawings have been made using conventional photographic techniques and although colors may appear different from actual colors due to light reflectance, they are as accurate as possible by conventional photography.

DESCRIPTION OF THE NEW VARIETY

The following is a detailed description of the new *Diascia* cultivar 'Aurora Cherry Blossom'. Data was collected in October 2013 in Santa Barbara, Calif. from a one year old plant which had been growing out of doors in a 20 cm diameter container. The color determinations are in accordance with the 2007 edition of The Royal Horticultural Society Colour Chart, except where general color terms of ordinary dictionary significance are used. The new *Diascia* variety named 'Aurora Cherry Blossom' has not been observed under all possible environmental conditions. Phenotypic differences may be observed with variations in environmental, climatic, and cultural conditions, without however, any difference in genotype.

Botanical classification:

*Genus.*—*Diascia.*

*Species.*—×*hybrida.*

*Denomination.*—'Aurora Cherry Blossom'.

*Common name.*—Twinspur.

*Commercial classification.*—Annual or perennial.

*Plant uses.*—Suitable for use in containers, borders and mass landscape plantings.

*Cultural requirements.*—Provide well-draining soil, full sun and regular water. Trimming when young will encourage strong basal branching.

*Hardiness.*—Hardy to USDA Zone 8.

*Parentage.*—Unnamed and unreleased seedlings from the inventors' breeding program.

Plant description:

*Blooming seasons.*—Spring, summer and fall.

*Plant habit.*—Compact upright habit.

*Plant form.*—Mounding form.

*Plant vigor.*—Vigorous.

*Plant density.*—Medium.

*Plant propagation method.*—Propagated using the method of vegetative tip cuttings.

*Production time.*—Six to eight weeks are required to produce a flowering plant in a quart or 10 cm diameter container. Ten to twelve weeks are required to produce a full flowering plant in a 1 gallon or 15 cm diameter container.

*Plant height* (*foliage mound*).—12 to 15 cm.

*Plant height* (*including flowers*).—25 to 30 cm.

*Plant width.*—25 to 30 cm.

*Root system.*—Fine and fibrous roots, profusely branching, and color is NN155D.

*Resistance and susceptibility to diseases and pests.*—No resistance or susceptibility to pests or disease is known to the inventor.

*Time to develop roots.*—10 to 14 days are needed to develop roots on an initial cutting.

*Special considerations.*—Encourage new branching by periodic pruning.

Stem: Stem produces 3 to 4 branching stems at 1 cm above surface. Each branching stem produces 1 to 2 nodal sub-branches.

*Flowering stems per plant.*—Approximately 100 during the year.

*Stem shape.*—Quadrilateral.

*Stem color.*—138B.

*Stem dimensions.*—15 cm in length, 3 mm in width.

*Internode length.*—Ranges from 2 cm to 3 cm.

*Stem surface.*—Smooth, glabrous.

Foliage:

*Number of leaves per branching stem.*—8 to 10.

*Leaf arrangement.*—Opposite.

*Leaf division.*—Simple.

*Leaf shape.*—Cordate.

*Leaf base.*—Cordate.

*Leaf apex.*—Acute.

*Leaf margin.*—Denticulate, teeth spaced at 3 mm, depth 0.5 mm.

*Leaf venation pattern.*—Pinnate.

*Vein color* (*both surfaces*).—138A.

*Leaf surface* (*both surfaces*).—Glabrous and semi-glossy.

*Leaf variegation*.—Absent.
*Leaf color* (*adaxial surface*).—137A.
*Leaf color* (*abaxial surface*).—138B.
*Leaf dimensions.*—2.5 cm in length, 1.5 cm in width.
*Leaf attachment*.—Sessile.

Inflorescence and flowers:
*Inflorescence type*.—Terminal raceme.
*Quantity per plant.*—5 to 8 on five months old plant.
*Inflorescence dimensions.*—12 cm in length; 4 cm in diameter.
*Quantity of flowers developed during inflorescence life.*—20 to 30.
*Quantity of fully open flowers at any time per inflorescence.*—8 to 15.
*Rate of flower opening.*—3 to 4 days from first color to fully open flower.
*Flower aspect*.—Outward-facing.
*Flowers persistent or self-cleaning*.—Self-cleaning.
*Flower shape*.—Personate with twin calcars (spurs).
*Flower dimensions.*—1.6 cm in height, 1.5 cm in width, 1.0 cm in depth.
*Flower color*.—N155B with eye 53C.
*Petals.*—5, basally fused.
*Petal shape*.—Orbicular.
*Petal surface*.—Glabrous.
*Petal margin*.—Entire.
*Petal apex*.—Obtuse.
*Petal base*.—Rounded.
*Petal dimensions* (*uppermost pair*).—6 mm in length, 4 mm in width.
*Petal dimensions* (*lateral pair*).—8 mm in length, 5 mm in width.
*Petal dimensions* (*lowest*).—15 mm in length, 12 mm in width.
*Petal color* (*adaxial surface*).—All petals N155B except 53C at base.
*Petal color* (*abaxial surface*).—Upper and lateral petals N155B, 53C at base; Lowest petal N155B only.
*Palate* (*pollinator landing spot*).—Located at base (where fused) of lowest petal; diameter 3 mm, color 70C.
*Corolla window color*.—N155B.
*Corolla window dimensions.*—2 mm in length and 2 mm in width.
*Calcar.*—2 in number.
*Calcar surface*.—Glabrous.
*Calcar dimensions.*—5 mm in depth and 2 mm in diameter.
*Calcar color*.—N155B as flower opens, becoming 53C as flower matures.
*Bud shape*.—Globose.
*Bud surface*.—Stipitate-glandular.
*Bud color* (*immediately prior to cracking color*).—146C.
*Bud dimensions.*—3 mm in length and 3 mm in width.
*Peduncle strength*.—Strong.
*Peduncle angle* (*where axillary*).—30 degrees from the vertical.
*Peduncle color.*—138B.
*Peduncle dimensions.*—3 cm to 5 cm in length, 1.5 mm in diameter.
*Peduncle shape*.—Quadrilateral.
*Peduncle surface*.—Smooth, lightly pubescent with 156D color hairs, length 0.3 mm.
*Pedicel strength*.—Medium.
*Pedicel angle.*—45 degrees away from the vertical.
*Pedicel color*.—Ranges between 161A and 168C.
*Pedicel dimensions.*—0.8 cm in length, 0.5 mm in width.
*Pedicel shape*.—Cylindrical.
*Pedicel surface*.—Smooth, glossy.

Calyx:
*Calyx shape*.—Stellate.
*Calyx color.*—146C.
*Number of sepals.*—5, unfused.
*Sepal color* (*adaxial and abaxial surfaces*).—146C.
*Sepal surface*.—Pubescent, tiny hairs, color is 156D.
*Sepal shape*.—Oblanceolate.
*Sepal dimensions.*—3 mm in length and 1 mm in width.
*Sepal apex*.—Acute.
*Sepal base*.—Truncate.
*Sepal margin*.—Entire.
*Blooming months*.—Flowers bloom April through November.
*Lastingness of flower*.—An individual flower lasts from 4 to 6 days on the plant.
*Flower fragrance*.—None.

Reproductive organs:
*Stamens.*—4.
*Stamen color*.—N186C.
*Stamen surface*.—Stipitate-glandular.
*Stamen dimensions.*—4 mm in length and 0.50 mm in width.
*Anthers*.—Tiny, ellipsoid, less than 1 mm in length, width; color 15B.
*Quantity of pollen*.—Slight.
*Color of pollen.*—15B.
*Pistil.*—1 in number.
*Stigma*.—Tiny, appears globose, and color is 197B.
*Style*.—Length is 1.5 mm and color is 156A.
*Ovary*.—Superior, globose, 1-2 mm in diameter, color close to 151C.
*Seed.*—None observed.

We claim:

1. A new and distinct cultivar of *Diascia* plant named 'Aurora Cherry Blossom' as described and illustrated herein.

* * * * *